United States Patent
Mizuochi

(10) Patent No.: US 7,429,107 B2
(45) Date of Patent: Sep. 30, 2008

(54) OPHTHALMIC PHOTOGRAPHY APPARATUS

(75) Inventor: Masaharu Mizuochi, Hamamatsu (JP)

(73) Assignee: Kowa Company Ltd. (JP)

( * ) Notice: Subject to any disclaimer, the term of this patent is extended or adjusted under 35 U.S.C. 154(b) by 202 days.

(21) Appl. No.: 11/071,715

(22) Filed: Mar. 3, 2005

(65) Prior Publication Data
US 2006/0126017 A1 Jun. 15, 2006

(30) Foreign Application Priority Data
Dec. 15, 2004 (JP) .............................. 2004-362112

(51) Int. Cl.
A61B 3/14 (2006.01)
A61B 3/10 (2006.01)
(52) U.S. Cl. ..................................... 351/206; 351/213
(58) Field of Classification Search .................. 351/206, 351/213
See application file for complete search history.

(56) References Cited

U.S. PATENT DOCUMENTS 5,557,350 A * 9/1996 Yano ........................... 351/208
5,936,706 A * 8/1999 Takagi ......................... 351/208
6,574,432 B2 * 6/2003 Nanjyo ......................... 396/18
2003/0071966 A1 * 4/2003 Matsumoto .................. 351/206
2004/0218145 A1 * 11/2004 Matsumoto .................. 351/214

* cited by examiner

Primary Examiner—Jordan M. Schwartz
Assistant Examiner—James C Jones
(74) Attorney, Agent, or Firm—Adams & Wilks

(57) ABSTRACT

An ophthalmic photography apparatus is provided in which focus and alignment can be adjusted over the whole period of infrared light-excited fluorescence photography. During alignment and focus adjustments, the brightness of index light sources used for such adjustments is increased. When the shutter is operated, the brightness of the index light sources is decreased, dimming the indexes. When the automatic gain control of the imaging device functions in the later phase of the photography, the brightness of the indexes is gradually increased. In the first part of the photography period, the indexes are dimmed to prevent the images thereof from showing up on the recording images, and are brightened in the later stages to make the indexes easier to see.

11 Claims, 4 Drawing Sheets

FIG. 4

| RING SLIT | EXCITER | BARRIER | LIGHT QUANTITY FOR OBSERVATION & PHOTOGRAPHY | PHOTOGRAPHIC MODE | TIMER | OBSERVATION MEANS | PHOTOGRAPHY MEANS | LED60 Obs. | LED60 Photo. | LED70 Obs. | LED70 Photo. |
|---|---|---|---|---|---|---|---|---|---|---|---|
| STANDARD 11 | None | None | 0 | Mydriatic | None | Ocular | (Still Image) Color CCD36 or 35mm | Red | Off | Red | Off |
| | Visible light-excited fluorescence | Visible light-excited fluorescence | +3 | Visible light-excited fluorescence | T1 | Infrared CCD35 | | Red | Off | Infrared | Off |
| | Infrared light-excited fluorescence | None | +6 | Infrared light-excited fluorescence | T2 | Infrared CCD35 | | Red | Off | Red | Off |
| | | | | | | Ocular | | Red | Off | Red | Off |
| | | | | | | Infrared CCD35 | | Red | Off | Infrared | Off |
| SMALL-PUPIL 12 | None | None | +1 | Non-mydriatic or Mydriatic | None | Infrared CCD35 | ✕ | Infrared | ✕ | Infrared | ✕ |
| | | | | Mydriatic | None | Ocular | (Still Image) Color CCD36 or 35mm | Red | Off | Infrared | Off |
| | Visible light-excited fluorescence | Visible light-excited fluorescence | +4 | Visible light-excited fluorescence | T1 | Ocular | | Red | Off | Red | Off |
| | | | | | | Infrared CCD35 | | Red | Off | Infrared | Off |
| | Infrared light-excited fluorescence | Infrared light-excited fluorescence | +5 | Infrared light-excited fluorescence | T2 | Infrared CCD35 | Still Image CCD37 Dynamic Image CCD35 | Infrared | Off | Infrared | Off |
| FLUORESCENCE 13 | | | | | | | | Infrared | On | Infrared | On |
| | Visible light-excited fluorescence | Visible light-excited fluorescence | +2 | Visible light-excited fluorescence | T1 | Ocular | (Still Image) Color CCD36 or 35mm | Red | Off | Red | Off |
| | | | | | | Infrared CCD35 | | Red | Off | Infrared | Off |

OPHTHALMIC PHOTOGRAPHY APPARATUS

BACKGROUND OF THE INVENTION

1. Field of the Invention

The present invention relates to an ophthalmic photography apparatus, and more particularly to an ophthalmic photography apparatus that can be used for non-mydriatic and mydriatic eye fundus color photography, visible light-excited fluorescence image photography, and infrared light-excited fluorescence image photography.

2. Description of the Prior Art

There are ophthalmic photography apparatuses such as fundus cameras and the like that, in addition to being capable of non-mydriatic and mydriatic color photography of the eye fundus, are also capable of photography by visible light-excited fluorescence (also designated as fluorescein angiography; FAG) and photography by infrared light-excited fluorescence (also designated as indocyanine green angiography; ICG). In each of these photographic modes, the apparatus is aligned and focused while observing the eye fundus, and the eye fundus is then photographed by operating a shutter switch.

The alignment and focusing prior to photography are done by projecting an alignment index and a focus index onto the eye to be examined and controlling the index light quantities according to the state of a photoelectric transducer receiving the image from the eye fundus (Japanese Laid Open Patent Publication No. 1987-41637), controlling the index brightness in accordance with the gain of an electronic camera (Japanese Laid Open Patent Publication No. 1997-66032), shielding the indexes during the fluorescence photography (Japanese Laid Open Patent Publication No. 1999-197113), shielding the indexes during photography (Japanese Laid Open Utility Model Publication No. 1993-102), or changing the wavelength of the observation light with the passing of the time during infrared light-excited fluorescence photography (Japanese Laid Open Patent Publication No. 2004-81255).

However, in the case of fundus cameras used to carry out infrared light-excited fluorescence photography in which a CCD is used for both observation and dynamic image photography, the focus index and alignment index that are not required for diagnosis are also recorded because the images that are observed are the same images that are recorded.

If, in order to avoid this problem, the indexes are not used during the infrared light-excited fluorescence photography, focusing and alignment have to be adjusted visually. Such visual adjustments may be possible during the initial phase when there is a sufficient level of infrared light-excited fluorescence, but become difficult in the later phase in which there is insufficient infrared light-excited fluorescence. Thus, during the transition from the initial to the later phase, the examiner has to switch the indexes on and off, using his or her own judgment, which increases the burden on the examiner when making a dynamic image recording.

It is therefore an object of the present invention to provide an ophthalmic photography apparatus that is able to carry out infrared light-excited fluorescence photography and recordings by securely enabling focusing and alignment adjustments to be made over the entire period of the infrared light-excited fluorescence photography.

SUMMARY OF THE INVENTION

The present invention provides an ophthalmic photography apparatus that has at least an infrared light-excited fluorescence photography mode and is capable of infrared light-excited fluorescence photography of an eye fundus. The ophthalmic photography apparatus comprises an index light source for forming a focus or alignment index projected onto the eye during infrared light-excited fluorescence photography; an imaging device for capturing an infrared light-excited fluorescence image of the eye fundus; a recorder for recording the captured infrared light-excited fluorescence images of the eye fundus as dynamic images; and a control means for controlling the index light source during infrared light-excited fluorescence photography to provide different quantities of light for when infrared light-excited fluorescence images are being recorded and not recorded.

When infrared light-excited fluorescence images are being recorded as moving images, it is possible to darken the focus and alignment indexes, which are not necessary for diagnosis, thereby substantially eliminating the index images from the recording images.

During the later phase of the infrared light-excited fluorescence photography wherein there is insufficient infrared light-excited fluorescence, an automatic gain control function on the imaging device comes into effect, or the quantity of light of the index light source is increased during recording. This increases the index brightness, making the alignment or focusing easy, thereby enabling stable infrared light-excited fluorescence photography and recording of dynamic images.

Further features of the invention, its nature and various advantages will be more apparent from the accompanying drawings and following detailed description of the invention.

BRIEF DESCRIPTION OF THE DRAWINGS

FIG. 4 is a table showing operations performed in each photographic mode.

DESCRIPTION OF THE PREFERRED EMBODIMENTS

An ophthalmic photography apparatus is realized in the form of a fundus camera that is able to carry out infrared light-excited fluorescence photography and captures the infrared light-excited fluorescence images of an eye fundus as moving images.

Figure 1:
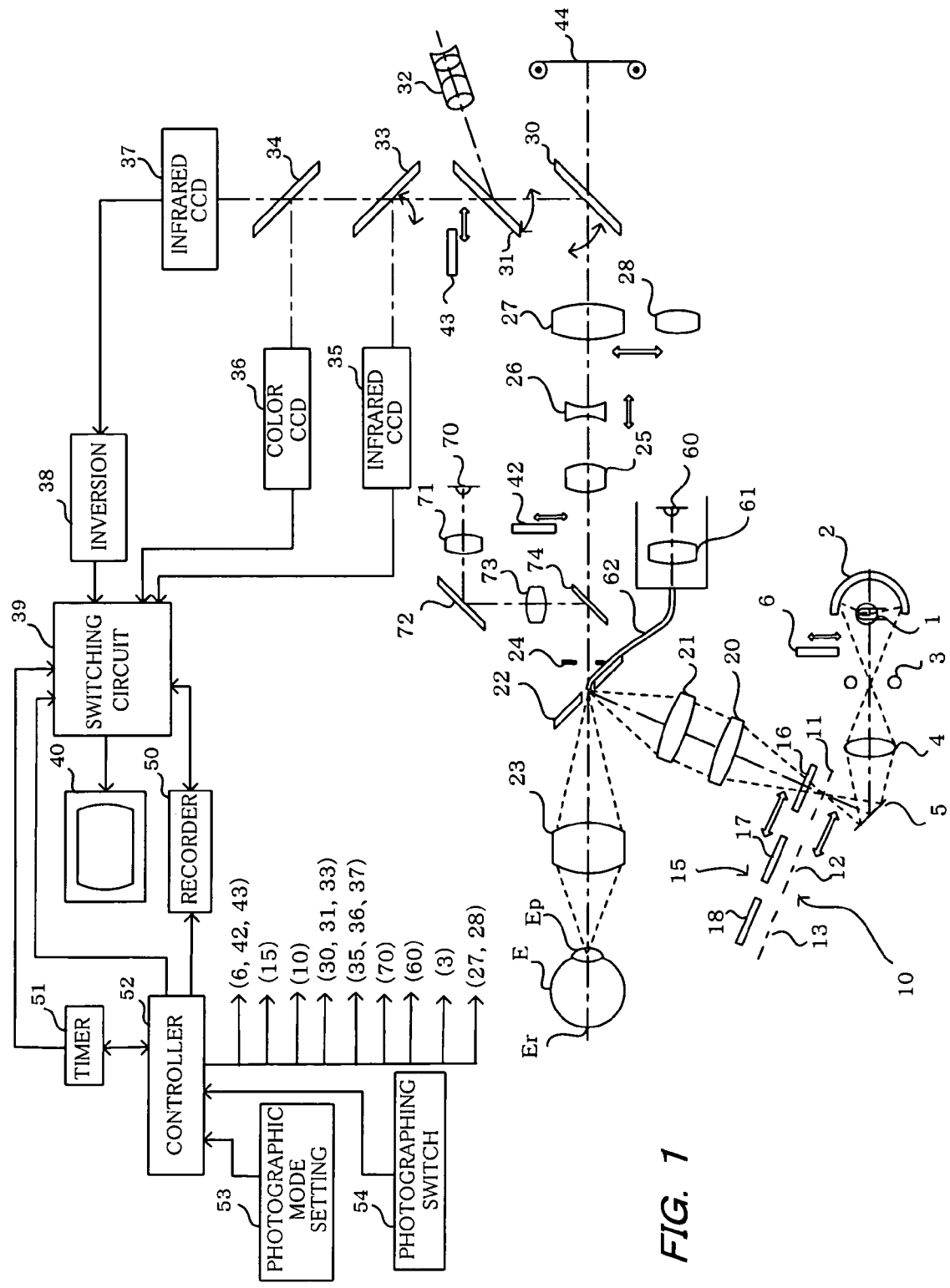
FIG. 1 is a schematic view showing an ophthalmic photography apparatus according to the present invention.

FIG. 1 shows such a fundus camera. A light beam from an observation light source 1 such as a halogen lamp or the like is concentrated by a concave mirror 2, passes through a strobe 3 serving as a photographing light source, and a condenser lens 4. The light beam is then reflected by a mirror 5, passes through relay lenses 20 and 21, and is reflected by an apertured total-reflection mirror 22. An objective lens 23 concentrates the beam thus reflected by the total-reflection mirror 22 to form an image at the pupil Ep of an eye E to be examined for illumination of the eye fundus Er.

During non-mydriatic examination, a filter 6 that transmits infrared light is inserted into the optical path of the fundus illumination system on the downstream side of the observation light source 1. A ring slit switcher 10 is provided that enables switching among a standard ring slit 11, a small-pupil ring slit 12 and a fluorescence ring slit 13. The standard ring slit 11 is the ring slit that is normally used; the small-pupil ring slit 12 is used when the patient's eye is not sufficiently dilated or when the patient is someone with a small pupil, such as a child; and the ring slit 13 is used during infrared light-excited fluorescence photography. These slits are imaged substantially at the location of the pupil Ep of the eye E, and the illuminating light falling incident on the ring-shaped aperture provides uniform illumination of the eye fundus.

Behind the ring slit switcher 10, there is located an illumination filter switcher 15 that can switch between a through-filter 16, a visible light-excited fluorescence exciter filter 17 that transmits blue light having a wavelength of 450 nm to 520 nm, and an infrared light-excited fluorescence exciter filter 18 that transmits infrared light having a wavelength of 700 nm to 800 nm. When the through-filter 16 is inserted into the optical path, all light is transmitted. The visible light-excited fluorescence exciter filter 17 is inserted into the optical path during visible light-excited fluorescence photography, and the infrared light-excited fluorescence exciter filter 18 is inserted during infrared light-excited fluorescence photography so that only infrared light is transmitted.

Light reflected from the eye fundus Er passes back through the pupil Ep, the objective lens 23, the aperture of the total-reflection mirror 22, a photography stop 24 on the optical path of the photographic optical system, focus lenses 25 and 26 and image-formation lens 27, and falls incident on return mirror 30. The image-formation lens 27 can be replaced by an image-formation lens 28 having a different magnifying power, thereby constituting a variable-power mechanism. Also on this photographic optical path, there is a barrier filter 42 that transmits visible light-excited fluorescence from the eye fundus and that can be inserted between a half-mirror 74 and the focus lens 25 during visible light-excited fluorescence photography.

Light from the fundus that is reflected by the return mirror 30 is reflected by a return mirror 31 onto an ocular lens 32 via which the examiner can observe the eye fundus image. When the filter 6 is inserted into the optical path and the return mirror 31 is retracted from the optical path, light from the eye fundus is reflected by a return mirror 33 onto an infrared observation optical system having an infrared CCD 35 serving as an imaging device that is sensitive to infrared light. Infrared images of the eye fundus captured by the infrared CCD 35 are displayed, via a switching circuit 39, on a monitor 40. The infrared CCD 35 has an automatic gain control (AGC) that is used to boost sensitivity when the image of the object being photographed darkens.

The infrared CCD 35 is used to capture images of the eye fundus during observation. The images captured are displayed on the monitor 40 as infrared dynamic images. This makes it possible for the examiner to carry out alignment and focusing adjustments while viewing the eye fundus image on the monitor 40. As described later, during infrared light-excited fluorescence photography, the infrared CCD 35 can also be used to capture dynamic (moving) infrared light-excited fluorescence images of the eye fundus.

For alignment purposes, the system of FIG. 1 is provided with an index light system comprising an alignment index light source 60, and optics in the form of a projection lens 61 and an optical fiber 62 that guides the index (index image) to the total-reflection mirror 22. The alignment index light source 60 comprises a two-color LED constituted by a visible-red-light LED and an infrared LED, located at the same position. The infrared LED is used during infrared light-excited fluorescence photography; in other photographic modes, the red-light LED is used. During observation using the infrared CCD 35, the infrared-light source can be used preferably as the alignment light source because it will not contract the eye, but since the wavelength will cause a change in the point at which the image is formed, the red-light LED is used for all photographic modes other than infrared light-excited fluorescence photography. There is a slight demerit of the pupil contracting as compared with infrared light. To prevent the pupil contracting, the red-light LED is preferably dimmed when in use.

The infrared or visible red light index thus formed by the alignment index light source 60 is projected onto the anterior part of the eye via the projection lens 61 and the optical fiber 62.

For focusing adjustment, an index light system comprising a focus index light source 70 and optics is provided that makes individual use of an infrared LED and a visible-red-light LED. The focus index (index image) used to adjust the focus is projected from the focus index light source 70 onto the eye fundus via optics in the form of lens 71, mirror 72, lens 73 and half-mirror 74. The focus index light source 70 makes individual use of two LEDs and a different optical system is used for each LED. The infrared LED is used in the infrared light-excited fluorescence photography mode, and the redlight LED is used in other photography modes. In FIG. 1, the focus index projection system is shown as using a red-light LED as the focus index light source 70; the apparatus also has a different optical system in which the infrared LED is used as the focus index light source 70, although it is not shown in FIG. 1.

During infrared light-excited fluorescence photography, a barrier filter 43 that transmits infrared light having a wavelength of 820 nm to 900 nm can be inserted into the optical path between return mirrors 31 and 33.

When the return mirror 33 is retracted from the optical path, the light from the eye fundus impinges on a dichroic mirror 34, which splits the beam into visible light and infrared light components. The visible light is reflected by the dichroic mirror 34 onto a color CCD 36 that is sensitive to visible light, while the infrared light is transmitted by the dichroic mirror 34 onto a CCD 37 that is sensitive to infrared light. The eye fundus image captured by the color CCD 36 is the image reflected by the dichroic mirror 34, so the image captured by the infrared CCD 37 is an inverse image of the eye fundus. Therefore, an image inversion circuit 38 is provided to carry out inversion processing of images from the color CCD 36 or infrared CCD 37 to vertically match the observed and captured images.

Using light emitted by the strobe 3 during photography, still images of the eye fundus can be obtained by the color CCD 36 and infrared CCD 37 and displayed on the monitor 40, via the switching circuit 39, and recorded and stored on a recorder 50. The recorder 50 can also record dynamic images from the infrared CCD 35.

When the return mirror 30 is retracted from the optical path, fundus images can be captured on photographic film 44 such as 35 mm film. Instead of the photographic film, an imaging device equivalent to the color CCD 36 can be used to capture the fundus images.

A timer 51 is provided to measure the time elapsed from intravenous injection of a fluorescent agent during infrared and visible light-excited fluorescence photography. The time signal from the timer 51 is input to a control circuit 52 (controller) comprised by a microcomputer or the like. A signal from a mode setting means 53 indicating the photographic mode, and a signal from a photographing switch (shutter) 54, are also input to the control circuit 52. Based on these signals, in accordance with each mode, the control circuit 52 controls the ring slit switcher 10 and the illumination filter switcher 15 to retract or insert the filter 6, barrier filters 42 and 43 and mirrors 30, 31 and 33, drives the CCDs 35, 36 and 37, controls the brightness of the alignment and focus index light sources 60 and 70, controls the operation of the strobe 3, and controls the magnification by selecting lens 27 or 28.

The operation of the ophthalmic photography apparatus thus configured will now be explained with reference to FIG. 2. The ophthalmic photography apparatus of this invention is capable of carrying out mydriatic and non-mydriatic photography, visible light-excited fluorescence photography and infrared light-excited fluorescence photography. Normal color photography is carried out in mydriatic or non-mydriatic mode.

Figure 2:
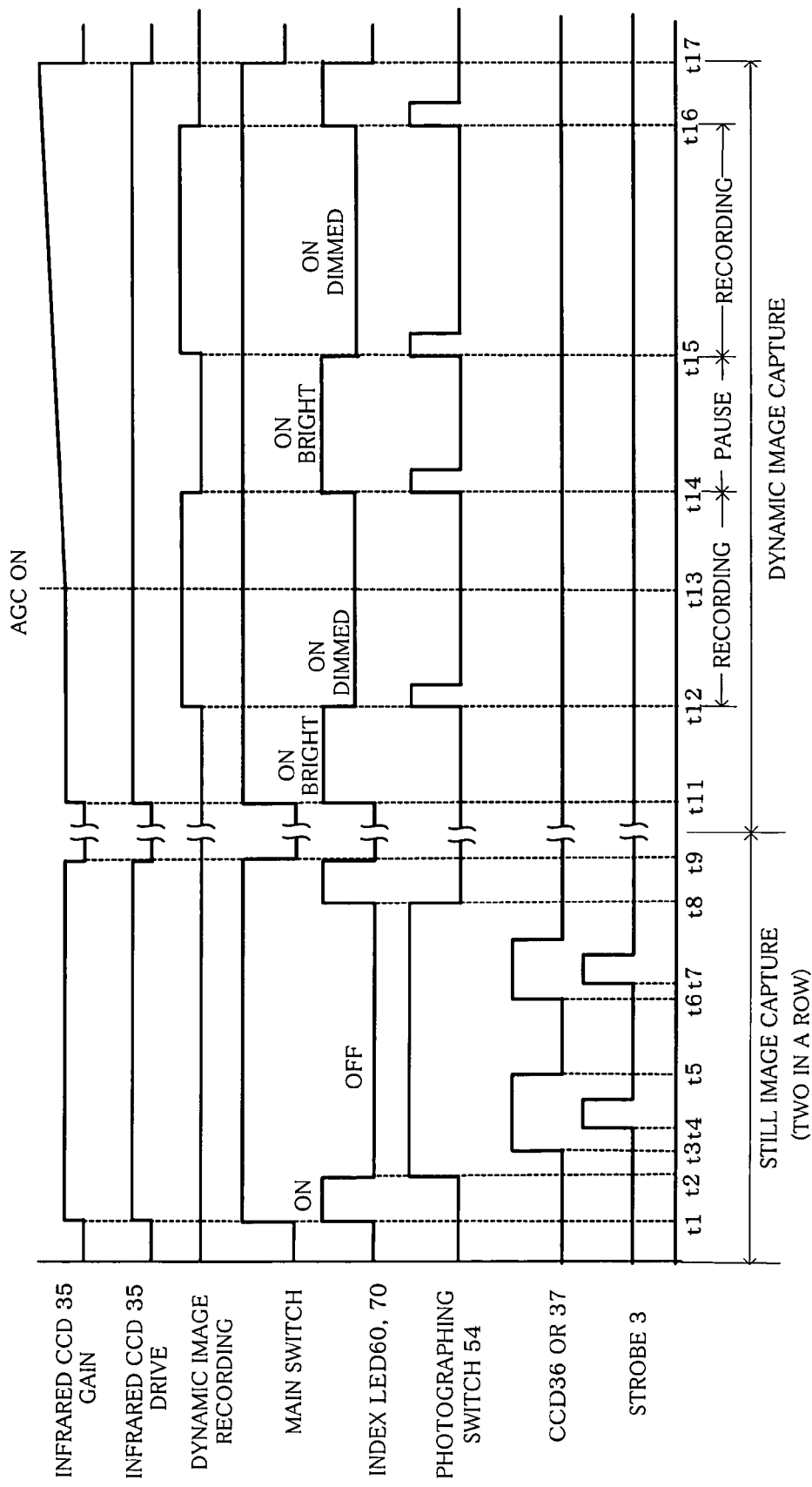
FIG. 2 is a timing chart showing sequences of capturing still and dynamic images of an eye fundus.

In FIG. 2, still image photography of the eye fundus was carried out from time t1 to time t9 in mydriatic, non-mydriatic, visible light and infrared light modes. Dynamic fundus image photography by infrared light-excited fluorescence was carried out from time t11 to time t17. When the main switch (not shown) is closed at time t1, the observation light source 1 comes on and, as indicated in FIG. 2, the alignment index light source 60 and focus index light source 70 come on and the infrared CCD 35 is driven with a prescribed gain.

In the case of mydriatic mode, drops of a mydriatic agent are put into the eye. When mydriatic mode is set using the mode setting means 53, the control circuit 52 retracts the filter 6 from the optical path and drives the ring slit switcher 10 to insert the standard ring slit 11 or small-pupil ring slit 12 into the optical path. Also, the through-filter 16 is selected and inserted into the optical path, and since the barrier filters 42 and 43 are for fluorescence mode photography, they are retracted from the optical path and the return mirrors 30, 31 and 33 occupy the positions shown in FIG. 1.

Light from the observation light source 1 that is reflected by the mirror 5 passes through the standard ring slit 11 (or the small-pupil ring slit 12), the through-filter 16, the relay lenses 20 and 21, and is reflected by the apertured total-reflection mirror 22 into the objective lens 23 to illuminate the eye fundus Er of the eye E. Reflected light from the eye fundus Er passes through the objective lens 23, total-reflection mirror 22, photographic stop 24, half-mirror 74, focus lenses 25 and 26 and the image-formation lens 27 and, via the return mirrors 30 and 31, falls incident on the ocular lens 32.

During mydriatic photography, the alignment index light source 60 and focus index light source 70 are lit by a red-light LED. The examiner adjusts the alignment and focus while observing the alignment and focus indexes via the ocular lens 32. When the alignment and focusing adjustments are completed, the shutter 54 is operated at time t2, at which the alignment index light source 60 and focus index light source 70 are switched off and the strobe 3 starts emitting light at time t4. The color CCD 36 is driven between times t3 and t5 before and after the strobe and the return mirror 33 is retracted from the optical path, whereby the color CCD 36 takes a still image of the eye fundus.

When the shutter 54 continues to be pressed, image capture continues, the color CCD 36 being again driven at time t6 and the strobe 3 emitting light at time t7, obtaining a second still image. When the shutter 54 is released at time t8, still image photography ends and the alignment index light source 60 and focus index light source 70 come on as the system goes into observation mode. The still images obtained are stored in the recorder 50.

Photography can be carried out using film 44, in which case the mirror 30 is retracted from the optical path. Infrared observation can be carried out without using the ocular lens 32, in which case the return mirror 31 is retracted from the optical path and fundus images are captured by the infrared CCD 35 as dynamic images which the examiner can view on the monitor 40 while adjusting the alignment and focus.

When the infrared CCD 35 is used for observation, the infrared LED of the focus index light source 70 lights, projecting an infrared focus index.

In the above mydriatic photography mode, as is also listed in FIG. 4, the standard ring slit 11 or small-pupil ring slit 12 is selected. The through-filter 16 is selected, so with respect to exciter filter, "None" is shown, and "None" is also shown with respect to barrier filter, since barrier filters 42 and 43 are withdrawn from the optical path. The quantity of light used for observation and photography is regulated by ring slit. In the case of a standard ring slit, the setting at which observation and photography takes place is "0", which is the default value; in the case of a small-pupil ring slit, the setting used is "+1". Since it is not fluorescence photography, "None" is also shown with respect to the timer used to measure the time that has elapsed from the intravenous injection of a fluorescence agent. The fundus is observed via the ocular lens 32 or via the images fed to the monitor 40 from the infrared CCD 35, and 35 mm film 44 or the color CCD 36 is used as the photography means. During observation, the red-light LEDs of the alignment index light source 60 and the focus index light source 70 are on, and off during photography. When the infrared CCD 35 is used for observation, the red-light LED of the alignment index light source 60 is dimmed, which is denoted by "Red-".

For non-mydriatic photography, the filter 6 is inserted into the optical path and small-pupil ring slit 12 is selected. The return mirror 31 is retracted from the optical path, and observation is carried out via the images fed to the monitor 40 from the infrared CCD 35. Continuous photography of still images is carried out by the same procedure shown in FIG. 2, and the still images thus obtained are recorded on film 44 or in the recorder 50. As shown in FIG. 4, observation is carried out only via the infrared CCD 35, and during observation, the red-light LED of the alignment index light source 60 is dimmed, so therefore emits visible red light at a muted level. On the other hand, the infrared LED of the focus index light source 70 lights, emitting infrared light for focus adjustment.

For visible light-excited fluorescence photography, the standard ring slit 11, small-pupil ring slit 12 or fluorescence ring slit 13 is selected and the observation light quantity is increased accordingly, to "+3", "+4" or "+2". Visible light-excited fluorescence exciter filter 17 is selected as the illumination filter, and barrier filter 42 as the photography filter.

When observation is carried out by viewing images sent to the monitor 40 from the infrared CCD 35, the filter 6 is inserted into, and the return mirror 31 is retracted from, the optical path. When observation is carried out via the ocular lens 32, the filter 6 is retracted from, and the return mirror 31 is inserted into, the optical path. When observation is done via the ocular lens 32, the visible light-excited fluorescence exciter filter 17 is inserted into the optical path.

When observation is done via the ocular lens 32, the red-light LEDs of the alignment index light source 60 and the focus index light source 70 are on, as shown in FIG. 4. When the infrared CCD 35 is used for observation, the red-light LED of the alignment index light source 60 is dimmed, and the infrared LED of the focus index light source 70 is on.

Upon completion of the alignment and focusing adjustments, a fluorescence agent is intravenously injected, the exciter filter 17 and barrier filter 42 are inserted into the optical path, and the timer 51 starts measuring elapsed time. After a prescribed time T1 has elapsed and the exciting light transmitted by the exciter filter 17 produces a visible light-excited fluorescence image in the fundus, the shutter 54 is pressed (at time t2 in FIG. 2), and the strobe 3 emits light. Depending on the position of the return mirror 30, visible light-excited fluorescence images will be photographed using the 35 mm film 44 or the color CCD 36. The same operation takes place each time the shutter 54 is operated, or the operation takes place continuously if the shutter is kept pressed. When the color CCD 36 is used to obtain still images, the return mirror 30 is inserted into the optical path and return mirrors 31 and 33 are retracted from the optical path. Still images photographed by the color CCD 36 are recorded and stored on the recorder 50.

During infrared light-excited fluorescence photography, observation cannot be done via the ocular lens 32, but only via images from the infrared CCD 35 appearing on the monitor 40. For observation via the monitor 40, standard ring slit 11 or fluorescence ring slit 13 is selected and the observation light quantity is increased to "+6" or "+5". The infrared LEDs of the alignment index light source 60 and the focus index light source 70 light, emitting infrared light. Infrared light-excited fluorescence exciter filter 18 is selected as the illumination filter, and barrier filter 43 as the photography filter. The infrared CCD 37 is used as the imaging device to take still images.

Upon completion of the alignment and focus adjustments at time t2, the fluorescence agent is intravenously injected, the barrier filter 43 is inserted, and the timer 51 starts measuring elapsed time. After a prescribed time T2 has elapsed and the exciting light transmitted by the exciter filter 18 produces an infrared light-excited fluorescence image in the fundus, the shutter 54 is pressed and the strobe 3 emits light (at times t4 and t7). At this time, the return mirror 30 is fixed in the position shown and return mirrors 31 and 33 are retracted, so infrared light-excited fluorescence images of the fundus are transmitted by the dichroic mirror 34 to fall incident on the infrared CCD 37 and be captured as still images. These images are vertically inverted by the image inversion circuit 38 and, via the switching circuit 39, are displayed on the monitor 40 as still images and recorded and stored on the recorder 50 as still images.

When infrared light-excited fluorescence photography is used to photograph and record dynamic images of the eye fundus, fluorescence ring slit 13 is selected and, as in the case of still image photography, infrared light-excited fluorescence exciter filter 18 is selected as the illumination filter and barrier filter 43 as the photography filter. The infrared LEDs of the alignment index light source 60 and the focus index light source 70 are on to each project an infrared index. Alignment and focus adjustments are carried out while using the monitor 40 to view the images of the alignment and focus indexes from the infrared CCD 35. In FIG. 2, this state is the segment from time t11 to time t12.

Upon completion of the alignment and focus adjustments at time t12, the fluorescence agent is intravenously injected, the barrier filter 43 is inserted, and the timer 51 starts measuring elapsed time. After a prescribed time T2 has elapsed and the exciting light transmitted by the exciter filter 18 produces an infrared light-excited fluorescence image in the fundus, the shutter 54 is pressed to start recording dynamic images, and infrared light-excited fluorescence images from the infrared CCD 35 are recorded and stored on the recorder 50 as dynamic images.

When the recording of dynamic images commences at time t12, the control circuit 52 reduces the light quantity of the alignment index light source 60 and focus index light source 70, reducing the index brightness. In FIG. 2, this state is shown as the index light sources 60 and 70 at point t12 changing from "Bright" to "Dimmed". In FIG. 4, this is shown as "Infrared-".

Thus, in the first phase in which there is a sufficient level of infrared light-excited fluorescence, the alignment and focus indexes are projected at a brightness that is not enough to show up on the observed images, thereby preventing the index images from becoming a hindrance to diagnosis without any real loss of image quality. When recording is not taking place, the brightness of the alignment and focus indexes can be increased to the same level used during normal observation (alignment), which is convenient for fundus camera operation during the recording of dynamic images.

In the later stage there is a decrease in the brightness of infrared light-excited fluorescence, for example, when time t13 is reached. At this time, the automatic gain control (AGC) of the infrared CCD 35 comes on and, as shown in FIG. 2, the gain increases with the passage of time to maintain the screen brightness at a constant level. As the sensitivity of the infrared CCD 35 is gradually amplified, the brightness of the alignment and focus indexes shown on the monitor 40 gradually rises. Since it is therefore possible to increase the screen brightness of the indexes in inverse proportion to the level of infrared light-excited fluorescence even if the infrared light-excited fluorescence images become darker, it does not hinder alignment and focus adjustments.

At time t14 in FIG. 2, the shutter 54 is operated, pausing the recording of dynamic images. At this time, the control circuit 52 again increases the light quantity of the alignment index light source 60 and focus index light source 70 to "Bright", making it possible to carry out any alignment and focus adjustments required at the same index brightness levels used during observation.

When the shutter 54 is again operated at time t15, the index light sources 60 and 70 are switched to "Dimmed", decreasing the light quantities. The light quantities of the index light sources at this point are the same as those at time t12, so the projected indexes are dim. However, as shown in FIG. 2, the sensitivity of the infrared CCD 35 increases in inverse proportion to the brightness of infrared light-excited fluorescence, so on the monitor 40, the indexes are clearly shown, enabling alignment and focus adjustments to be readily carried out even during the later stage of the infrared light-excited fluorescence photography.

Figure 3:
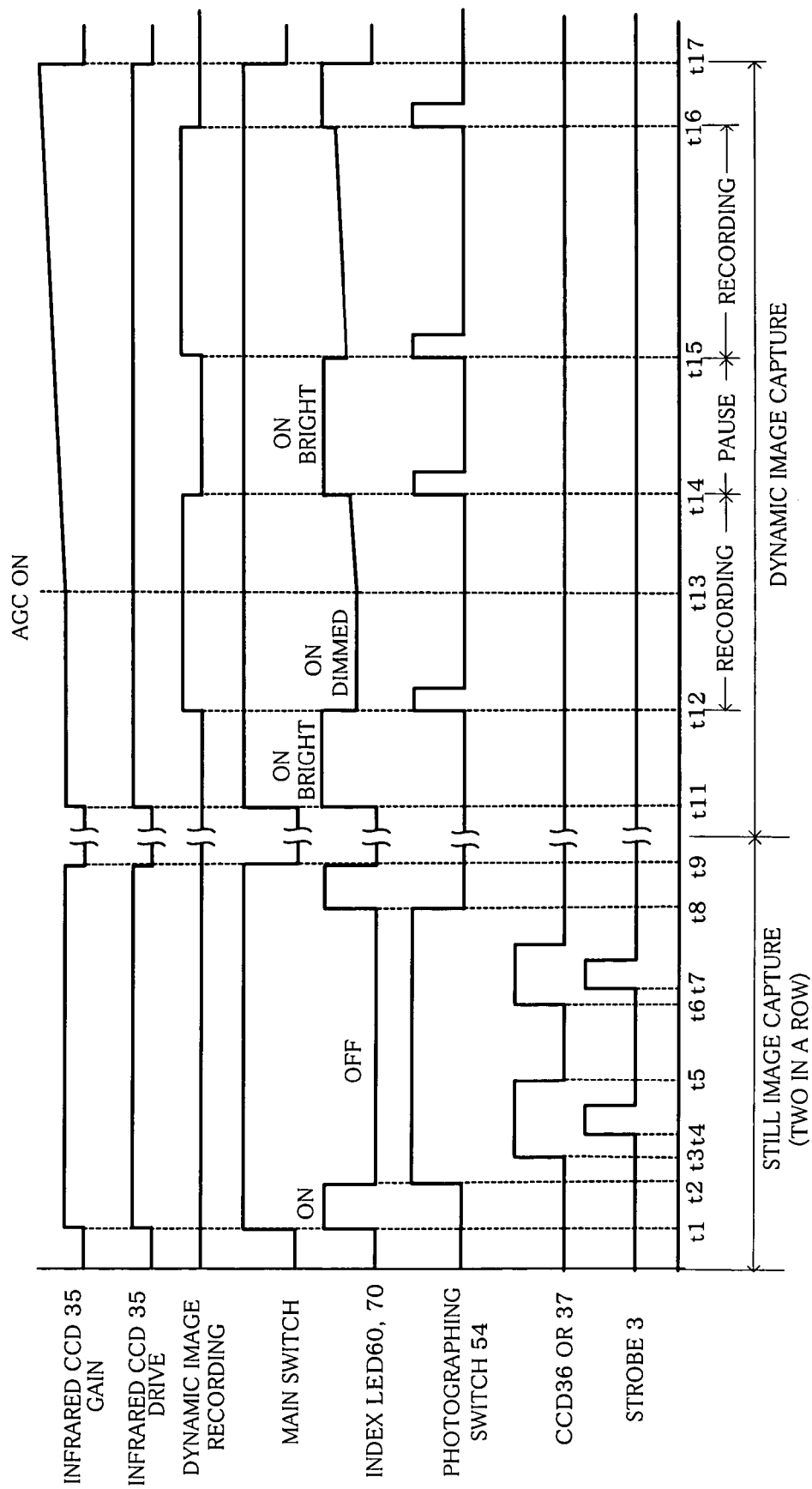
FIG. 3 is another timing chart showing sequences of capturing still and dynamic images of an eye fundus.

In the above embodiment, the AGC function of the infrared CCD 35 is utilized to increase the screen brightness of the alignment and focus indexes. The effect can be further increased by using the control circuit 52 to increase the light quantity of the index light sources. An example of this is shown in FIG. 3, in which, from time t13 at which the AGC comes into effect, the brightness of the projected alignment and focus indexes gradually increases under the control of the control circuit 52 (from time t13 to t14, and from time t15 to t16). This makes it possible to obtain indexes that become brighter in the later phase of the infrared light-excited fluorescence, ensuring that alignment and focus adjustments can be readily accomplished in the later stages.

In the above embodiment, the increase in the light quantities of the index light sources during recording takes place from the point at which the AGC comes on. Instead, however, the brightness of the index light sources 60 and 70 can be increased during recording with the passage of time after the elapse of a prescribed time from the commencement of infrared light-excited fluorescence photography, as measured by the timer 51.

Thus, when there is enough infrared light-excited fluorescence to carry out focus and alignment adjustments, it is possible to prevent images of alignment and focus indexes showing up on recording images. On the other hand, when there is not enough infrared light-excited fluorescence for such adjustments, the alignment and focus indexes can be made to show up clearly on the images to enable the adjustments to be made.

Dynamic images can be recorded during both phases of the infrared light-excited fluorescence photography process. However, for clinical diagnostic purposes, it is the dynamic images of the first phase that are important. In the invention, it is possible to prevent images of the indexes appearing on the recording images during the first phase. On the other hand, the indexes can be brightened in the later phase to facilitate the alignment and focus adjustments, thereby ensuring stable dynamic image capture and recording in infrared light-excited fluorescence photography.

What is claimed is:

1. An ophthalmic photography apparatus that has at least an infrared light-excited fluorescence photography mode and is capable of infrared light-excited fluorescence photography of an eye fundus, the ophthalmic photography apparatus comprising:
   an index light source that forms a focus or alignment index projected onto the eye during infrared light-excited fluorescence photography;
   an imaging device that captures an infrared light-excited fluorescence image of the eye fundus;
   a recorder that records the captured infrared light-excited fluorescence images of the eye fundus as dynamic images; and
   control means for controlling the index light source during infrared light-excited fluorescence photography to provide different quantities of light for when infrared light-excited fluorescence images are being recorded and not recorded;
   wherein during recording the control means changes the quantity of light of the index light source with the passage of time after the elapse of a prescribed time from a commencement of infrared light-excited fluorescence photography.

2. An apparatus according to claim 1; wherein the index is gradually brightened with the passage of time.

3. An ophthalmic photography apparatus operable in an infrared light-excited fluorescence photography mode to photograph an eye fundus, the apparatus comprising:
   an index light system that forms an index image for focusing or alignment purposes and projects the index image onto the eye during infrared light-excited fluorescence photography;
   an imaging device that captures infrared light-excited fluorescence images of the eye fundus;
   a recorder that records the captured infrared light-excited fluorescence images of the eye fundus as dynamic images; and
   a controller that controls the index light system during infrared light-excited fluorescence photography to make the index image dimmer during recording of infrared light-excited fluorescence images than when infrared light-excited fluorescence images are not being recorded so that the index image does not appear in the recorded infrared light-excited fluorescence images.

4. An ophthalmic photography apparatus according to claim 3; wherein the index light system includes an index light source for forming the index image, and optics for projecting the index image onto the eye.

5. An ophthalmic photography apparatus according to claim 4; wherein the imaging device has an automatic gain control; and the controller maintains the index light source at a constant quantity of light, during recording by the recorder, when the automatic gain control is functioning.

6. An ophthalmic photography apparatus according to claim 4; wherein the imaging device has an automatic gain control; and the controller changes the quantity of light of the index light source, during recording by the recorder, when the automatic gain control is functioning.

7. An ophthalmic photography apparatus according to claim 4; wherein during recording by the recorder, the controller changes the quantity of light of the index light source with the passage of time after the elapse of a prescribed time from commencement of infrared light-excited fluorescence photography.

8. An ophthalmic photography apparatus according to claim 3; wherein the controller gradually brightens the index image with the passage of time.

9. An ophthalmic photography apparatus according to claim 3; wherein the imaging device has an automatic gain control; and the controller maintains constant the brightness of the index image, during recording by the recorder, when the automatic gain control is functioning.

10. An ophthalmic photography apparatus according to claim 3; wherein the imaging device has an automatic gain control; and the controller changes the brightness of the index image, during recording by the recorder, when the automatic gain control is functioning.

11. An ophthalmic photography apparatus according to claim 3; wherein during recording by the recorder, the controller changes the brightness of the index image with the passage of time after the elapse of a prescribed time from commencement of infrared light-excited fluorescence photography.

* * * * *